(12) United States Patent
Beyar et al.

(10) Patent No.: US 6,371,979 B1
(45) Date of Patent: *Apr. 16, 2002

(54) STENT DELIVERY SYSTEM

(75) Inventors: Mordechay Beyar, Tel Aviv; Oren Globerman, Holon; Rafael Beyar, Haifa, all of (IL)

(73) Assignee: IntraTherapeutics, Inc., St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/803,324

(22) Filed: Feb. 21, 1997

Related U.S. Application Data (63) Continuation of application No. 08/607,442, filed on Feb. 27, 1996, now abandoned, which is a continuation of application No. 08/355,811, filed on Dec. 14, 1994, now abandoned, which is a continuation of application No. 08/009,470, filed on Jan. 27, 1993, now abandoned.

(51) Int. Cl.[7] ................................................. A61F 2/06
(52) U.S. Cl. ........................ 623/1.12; 623/1.17; 623/1.2; 623/1.22; 606/108
(58) Field of Search ............................. 606/108; 623/1, 623/12, 1.11, 1.12, 1.17, 1.2, 1.22

(56) References Cited

U.S. PATENT DOCUMENTS

| | | | |
|---|---|---|---|
| 4,512,338 A | 4/1985 | Balko et al. | |
| 4,553,545 A | * 11/1985 | Maass et al. | ................ 604/104 |
| 4,768,507 A | 9/1988 | Fischell et al. | |
| 4,878,906 A | * 11/1989 | Lindemann et al. | ........ 606/108 |
| 4,913,141 A | * 4/1990 | Hillstead | .................... 606/108 |
| 5,019,090 A | 5/1991 | Pinchuk | |
| 5,071,407 A | 12/1991 | Termin et al. | |
| 5,147,370 A | 9/1992 | McNamara et al. | |
| 5,160,341 A | 11/1992 | Brenneman et al. | |
| 5,221,261 A | 6/1993 | Termin et al. | |
| 5,242,451 A | 9/1993 | Harada et al. | |
| 5,246,445 A | 9/1993 | Yachia et al. | |
| 5,372,600 A | 12/1994 | Beyar et al. | |
| 5,378,239 A | 1/1995 | Termin et al. | |
| 5,496,277 A | 3/1996 | Termin et al. | |
| 5,814,052 A | 9/1998 | Nakao et al. | |

FOREIGN PATENT DOCUMENTS

WO        91/16005        10/1991

* cited by examiner

*Primary Examiner*—Michael H. Thaler
(74) *Attorney, Agent, or Firm*—Merchant & Gould P.C.

(57) ABSTRACT

This invention is directed to a stent delivery system for implanting a flexible, generally cylindrical, expandable, coiled stent. The system comprises a catheter defining at least one lumen and having at least two longitudinally displaced openings or sets of openings ,a flexible, self-expandable coiled stent having discrete proximal and distal end sections, said stent being wound circumferentially around said catheter and coils of the stent being more closely wound at the proximal and/or distal end sections, and one or two release wires cooperating with restraining means so that as the release wire or wires are with-drawn proximally, the proximal and distal end sections of the stent are released in such a manner that coils of the stent unwind and the length of the unwound stent is not substantially less than the length of the portion of the unreleased stent that is not more closely wound.

10 Claims, 9 Drawing Sheets

STENT DELIVERY SYSTEM

This application is a continuation of application Ser. No. 08/607,442, filed Feb. 27, 1996, now abandoned which is a continuation of Ser. No. 08/355,811 filed Dec. 14, 1994, now abandoned, which is a continuation of Ser. No. 08/009,470 filed Jan. 27, 1993, now abandoned.

FIELD OF THE INVENTION

This invention is directed to a device for the treatment of constricted ducts in human bodies. More particularly, this invention is directed to a vascular or coronary stent and a system for inserting or implanting it.

BACKGROUND OF THE INVENTION

Numerous stents are known to be useful for insertion into the body. Known stents include balloon expandable stents, as represented, for example, by U.S. Pat. Nos. 5,108,416, 4,735,665, and 4,739,762, as well as self-expandable stents formed from coiled material. See, for example, U.S. Pat. Nos. 4,913,141, 4,768,507, and 4,580,568. With regard to any of these stents, particularly the coiled stents, expansion normally causes the length of the stents to decrease during insertion or implantation. This can be a distinct disadvantage with regard to precise positioning of such stents. There is a definite need for stents that either shorten only a minimal amount or shorten in a predictable manner, to facilitate more precise positioning within the body.

OBJECTS OF THE INVENTION

It is an object of this invention to provide a stent for treating constricted ducts.

It is also an object of this invention to provide a vascular or coronary stent and a system for deploying same.

It is a further object of this invention to provide a wound coil stent which does not significantly shorten along its length during deployment of the stent, or shortens in a predictable manner.

These and other objects of the invention will become more apparent in the discussion below.

DETAILED DESCRIPTION OF THE INVENTION

This invention is directed to a stent and stent delivery system that overcomes the disadvantages of prior art stents and stent delivery systems in that the stent does not appreciably shorten in its length relative to its pre-mounted length, or shortens in a predictable manner, during deployment of the stent. Also, the center of the stent either stays in the same place it was before release from the catheter or is predictably relocated. The stent delivery system comprises a coiled stent removably fixed to a delivery catheter. The stent is affixed to the delivery catheter at three separate points, that is, at the middle of the stent and at the distal and proximal ends of the stent, or at two separate points, the proximal and distal ends of the stent. At one or both of the ends where the stent is affixed to the catheter, the stent is more tightly wound, i.e., has more pitch per unit length. The stent is preferably released by sequential release of the stent at its distal end, at its proximal end, and, optionally, then at its middle. It is also possible to release first its proximal end, then its distal end, and finally its middle. When the stent is more tightly wound only at one end, the stent is only held at two points. Then, the center of the stent relocates in predictable fashion as the stent unwinds after release.

Figure 1:
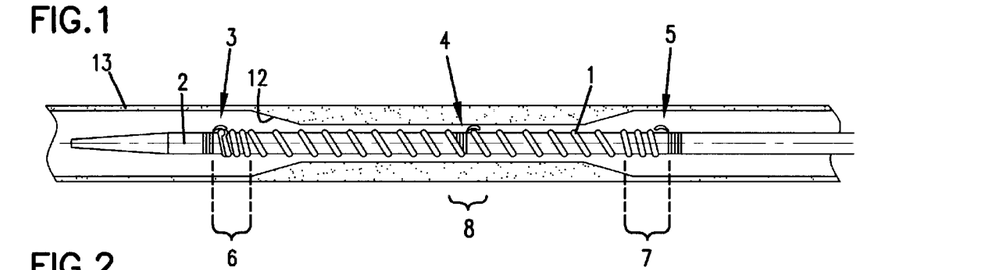
FIGS. 1 to 5 represent partially cross-sectional views of an embodiment of the invention shown in successive stages of release.

The stent and stent delivery system of the invention intended for vascular or coronary application can perhaps be more appreciated by making reference to the drawings. In FIG. 1, the stent delivery system, preferably for vascular application, is in its pre-release condition where the coiled stent 1 is affixed to delivery catheter 2 at distal fixation point 3, middle fixation point 4, and proximal fixation point 5. Stent 1 is more tightly wound at distal section 6 and proximal section 7.

The stent 1 can be releasably affixed to catheter 2 by use of several different methods known in the art. Preferably the affixation consists of a loop locking mechanism 10 that extends over a respective portion, that is, one or more coils, of catheter 1 through an opening in the outer surface of catheter 2 to be restrained by one or more restraining means or wires within one or more lumens within catheter 2. Such restraining means are discussed in more detail below.

It is also within the scope of the invention that other locking or restraining means could be employed to affix stent 1 to catheter 2. For example, a system such as is shown in U.S. Pat. No. 4,913,141, or in co-pending, commonly assigned U.S. patent applications Ser. No. 07/781,174, filed Dec. 11, 1991, Ser. No. 07/805,737, filed Dec. 10, 1991, and Ser. No. 07/827,031, filed Jan. 24, 1992, all of which are incorporated herein by reference, could be employed as well.

Figure 2:
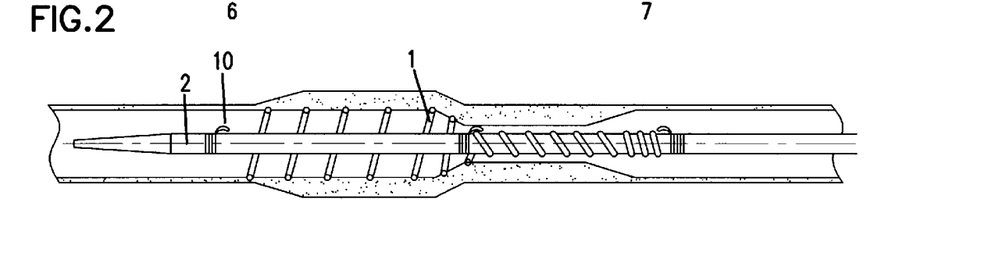
Figure 3:
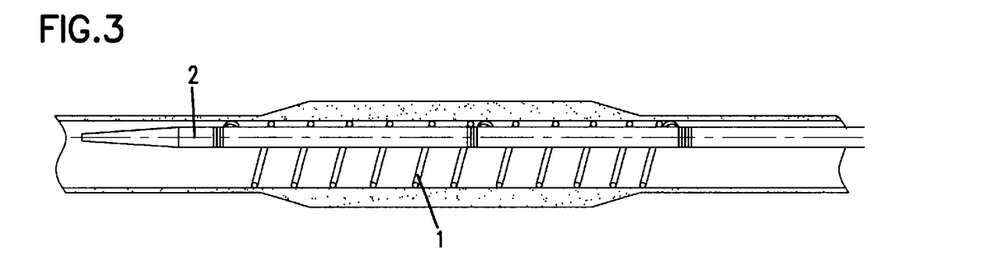
Figure 4:
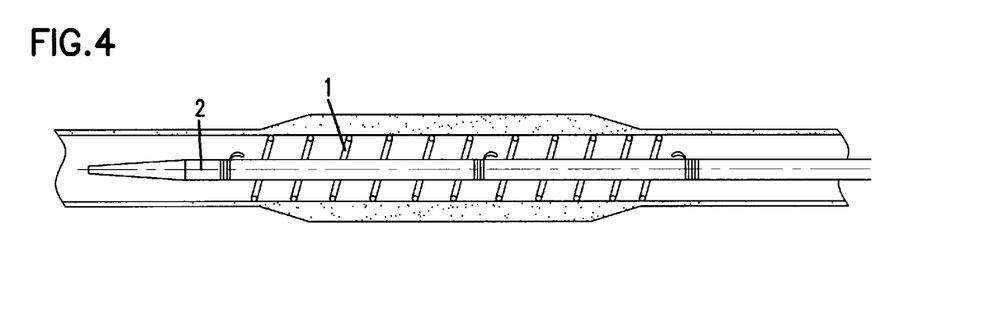

To take full advantage of the stent delivery system described herein, stent 1 should be sequentially released from catheter 2, as shown in FIGS. 2 to 4. Preferably the distal section 6 of stent 1 is released, the proximal section 7 is released, and then the middle section 8 of stent 1 is released at fixation point 4. After release of the distal end of the stent 1, stent 1 starts to open, i.e., unwind, from the distal side towards the middle. Contact of the stent wire with the inner wall 12 of blood vessel 13 forms an indentation or groove in vessel wall 12 with a pitch corresponding to that of the tightly wound stent. However, because the rotating stent increases in diameter, its length decreases slightly in the direction of the middle, and the tight winding of the end of the stent disappears. The middle section 8 of released stent 1 will be positioned at, or substantially identically at, the same place as before stent 1 was released, i.e., at fixation point 4. Following release at all three fixation points, catheter 2 is withdrawn, as shown in FIG. 5.

Figure 5:
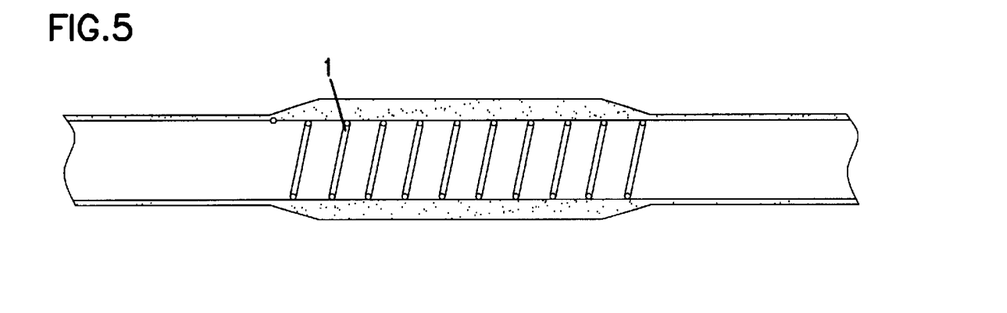

The unwound, released stent 1 shown in FIG. 5 has a longitudinal length substantially identical to the pre-mounted length of the stent. This length is also equal to approximately 55 to 110%, preferably from about 60 to 100%, of the total length of the wound, pre-release stent shown in FIG. 1. This relationship will vary dependent upon many factors, such as the tightness of the coils, the stent material, the body tube diameter prior to the stent deployment, and the stent diameter. The middle of the released stent will be positioned at substantially the same location as the coiled stent prior to release, assuming the catheter itself hasn't moved as the stent releases.

The winding of stent 1 is configured so that the stent is more closely wound at fixation points 3 and 5, although stent 1 as released expands to uniform winding, as shown in FIG. 5. For example, if the winding of released stent 1 might consist of 15 coils per inch of length, the compressed winding at points 3 and 5 could consist of 20 to 45 coils per inch. It is within the scope of the invention that the tightness, i.e., the distance between the coils, of the coils as well as the length of the closely wound coil sections could be adjusted dependent upon the particular application intended. By the appropriate combination of wound and more tightly wound coils, one skilled in the art should be able to easily achieve situations wherein the released stent 1 will have substantially the same length as pre-mounted coil 1.

Figure 6:
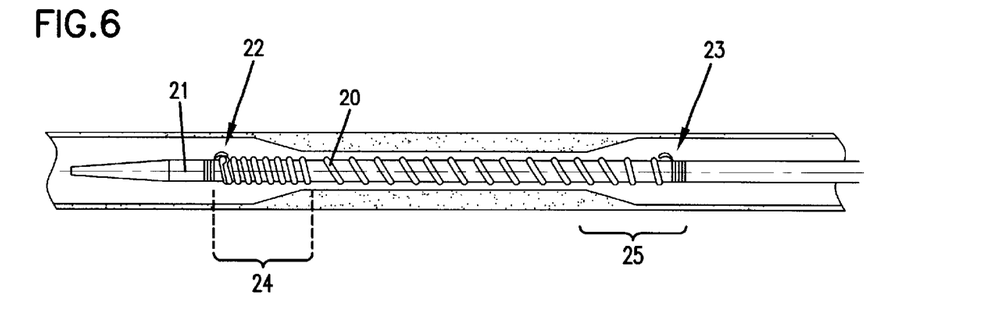
FIGS. 6 to 9 represent partially cross-sectional views of another embodiment of the invention shown in successive stages of release.

Another embodiment of the invention, preferably intended for coronary use, is shown in FIGS. 6 to 9. In FIG. 6, the stent delivery system is shown in its pre-release condition where the coiled stent 20 is affixed to delivery catheter 21 at distal fixation point 22 and proximal fixation point 23. Stent 20 is more tightly wound at distal section 24, and stent 20 is releasably affixed to catheter 21 by the methods discussed above and below. The differences in winding between distal section 24 and the remainder of stent 20 is similar to the differences described above for stent 1. It is within the scope of the invention that stent 20 may instead be more tightly wound only at proximal section 25 or at both distal section 24 and proximal section 25; however, preferably stent 20 is more tightly wound at distal section 24.

Figure 7:
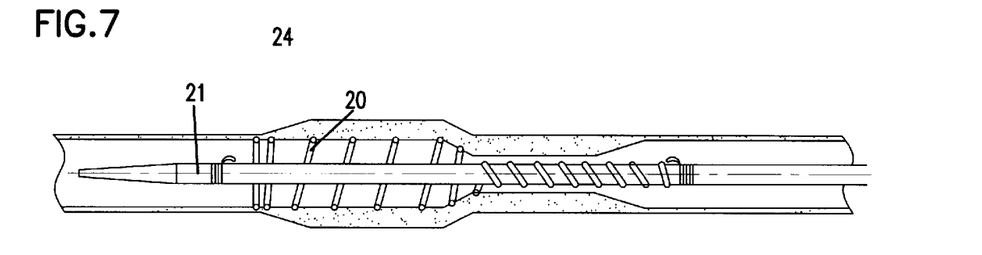
Figure 8:
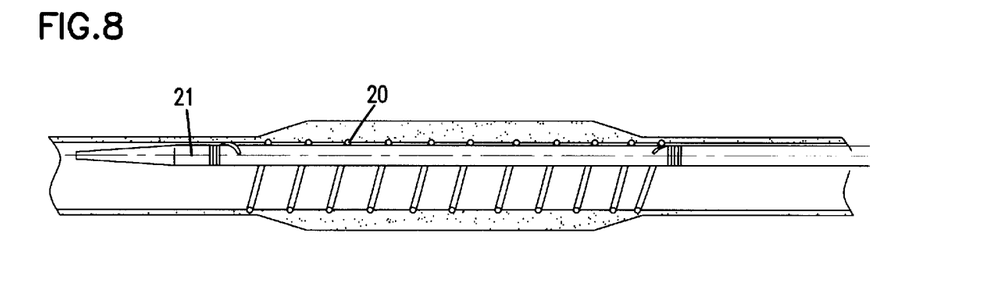

Stent 20 is released from catheter 21 by sequential release of distal section 24 of stent 20 and then proximal section 25. When distal section 24 is released, stent 20 begins to unwind and expand radially, starting from the distal end, and the individual coil expansion moves in the proximal direction, as shown in FIGS. 7 and 8. Once proximal section 25 is released (FIG. 9), stent 20 is substantially expanded throughout its length. The longitudinal length of released stent 20 is substantially the same as the length of the pre-released stent, or the less dense portion of the mounted stent, which is, in turn, from about 55 to 110%, preferably from about 60 to 95%, of the total length of wound, pre-release stent 20. Optionally, if proximal section 25 was more tightly wound, proximal section 25 could be released first, whereby the coil unwinding would move in the distal direction, and then distal section 24 would be released.

When the stent 20 is affixed to the delivery catheter 21 at only two points, the release sequence preferably depends upon which end or ends of the stent are more tightly wound. One of sections 24 and 25 can be more tightly wound, and then that end of the stent is released first. Regardless of which closely wound end is released first, the middle of released stent 20 should be positioned in substantially the same place, if not the identical place, as the middle portion of the less tightly wound section of the unreleased stent, assuming that the catheter doesn't move during the stent release. At the very least with this configuration it will be possible to reliably predict where the middle of the released stent will be located.

The stent delivery system shown in FIGS. 6 to 9 may comprise one or two release wires. When one release wire is used, first distal section 24 and then proximal section 25 are released. However, if it is desired (1) to release both sections 24 and 25 simultaneously or more closely together than would be possible if only one release wire were used or (2) to release proximal section 25 before distal section 24, then two release wires would be used. Also, as noted above, in another embodiment of the invention proximal section 25 may be more closely wound than the remainder of stent 20, including distal section 24. Preferably proximal section 25 would then be released at the same time as or before distal section 24.

Figure 9:
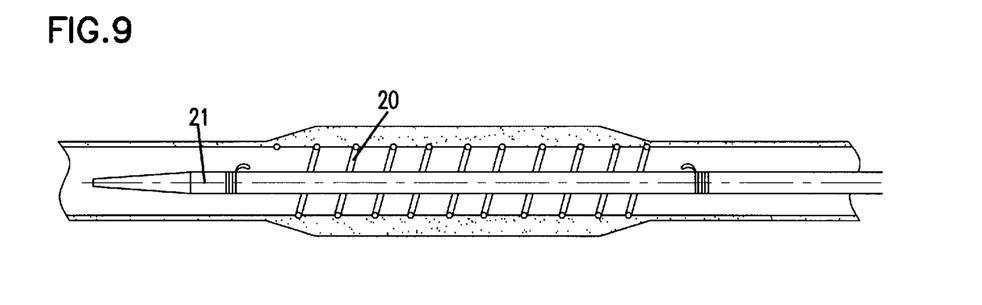
Figure 9A:
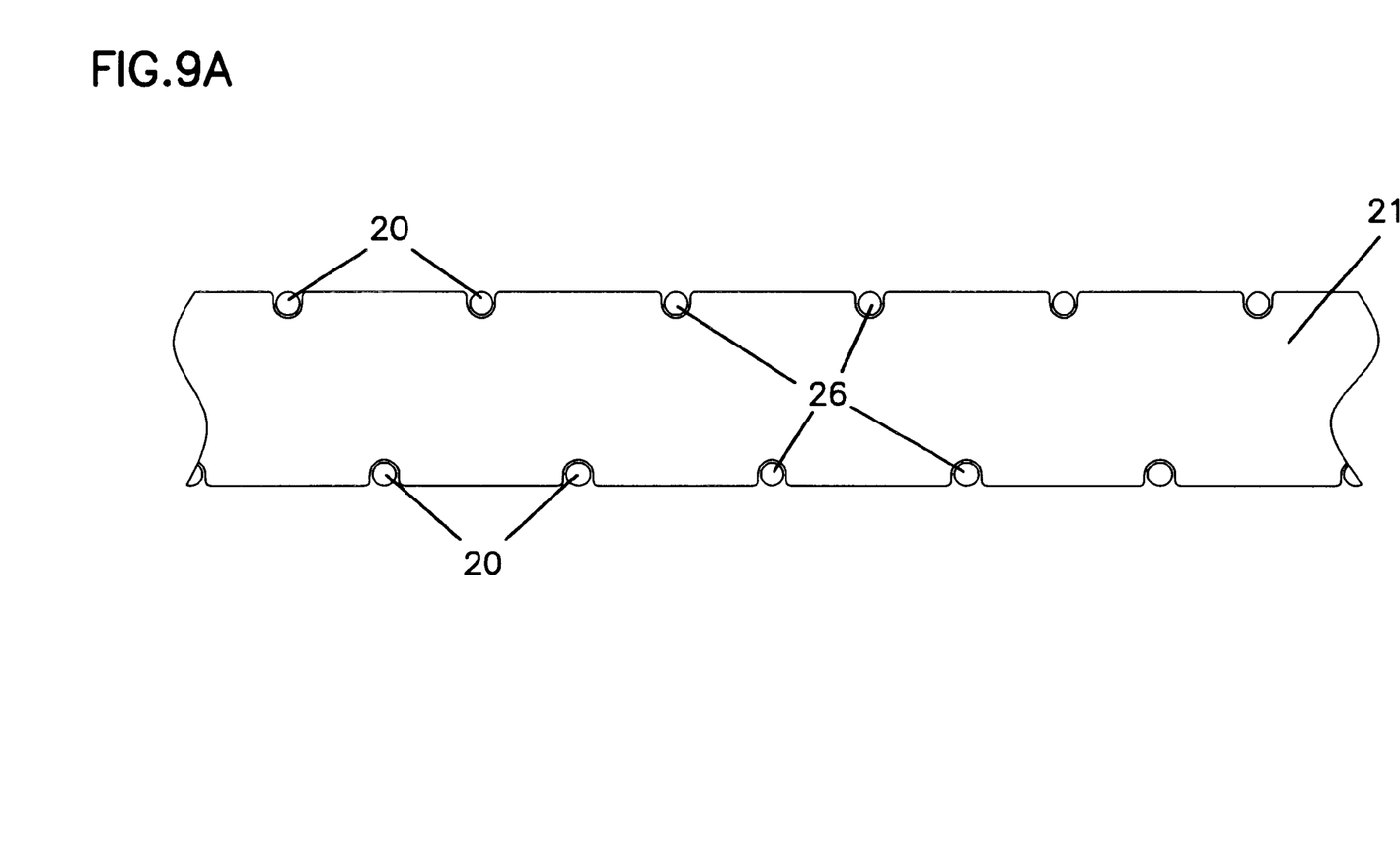
FIG. 9A is an enlarged cross-sectional view of a portion of the stent delivery system of FIGS. 6–9.

The catheter itself could be comprised of any polymeric material suitable for such catheters. Useful materials include polyethylene, polyurethane, polypropylene, and co-polymers therewith. Preferably catheter 2 or 21 has a decreased diameter in the area of the catheter where stent 1 or 20 is mounted, to enable the delivery system to have a lower profile at that point, comparable to the diameter of the remainder of the catheter 2 or 21. Also, catheter 2 or 21 preferably has grooves 26 on its outer surface that correspond to the coils of wound stent 1 or 20, as shown in FIG. 9A.

Likewise, the release wires useful herein can be comprised of any physiologically acceptable polymer or metal suitable for such purpose. Stainless steel wires are especially useful in this regard.

Figures 10, 11:
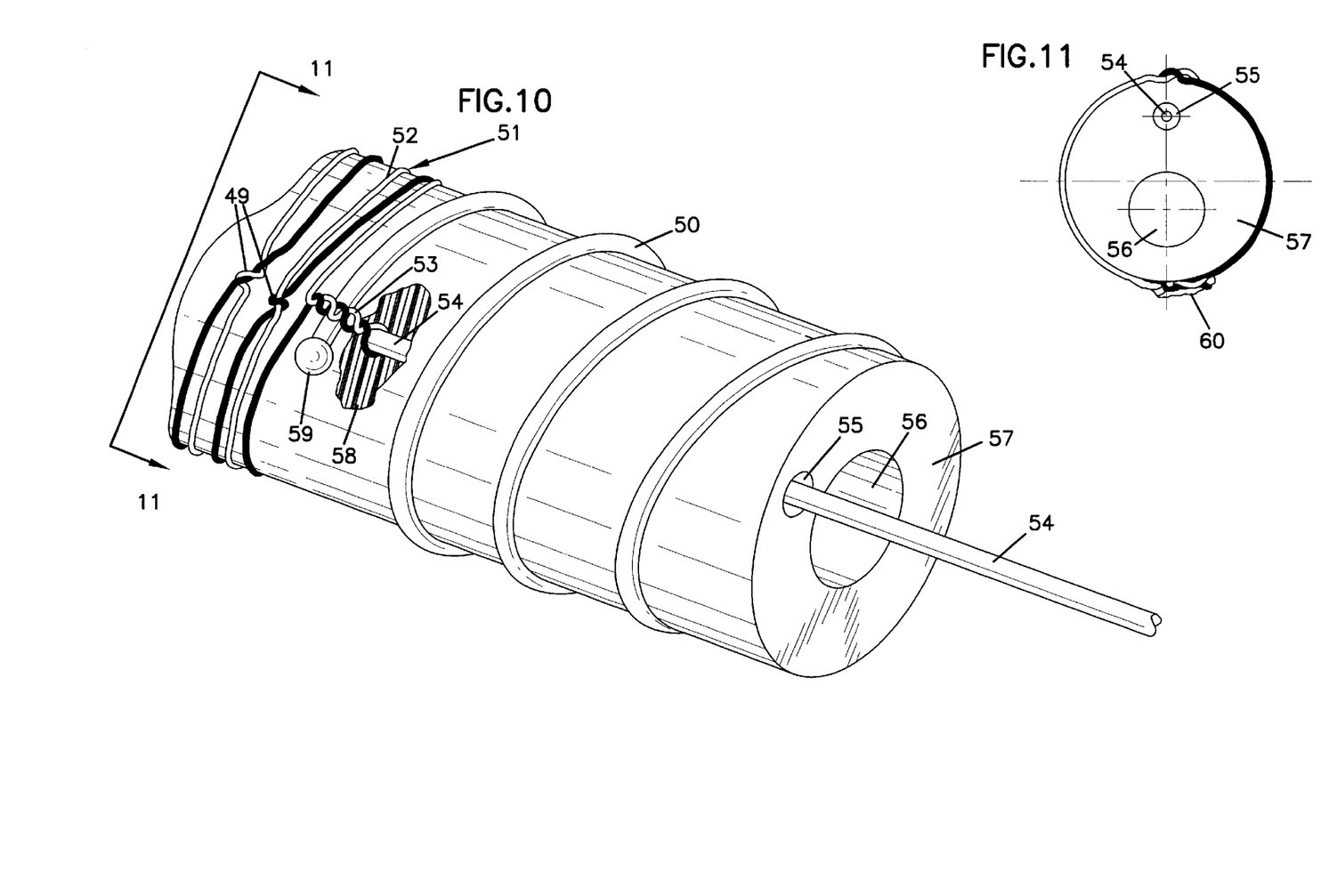
FIGS. 10 and 12 represent oblique, partially cross-sectional views of a fixation point.
FIG. 11 represents a cross-sectional view of a band portion.

In the aspect of the invention set forth in FIG. 10, the respective distal and proximal ends and the middle of a stent 50 are restrained by a restraining means 51 comprising a band 52 and a fixation member 53. Band 52 and fixation member 53 are comprised of a continuous flexible fiber that extends through opening 58 and is looped around release wire 54, and is then intertwined to form fixation member 53, which passes over the external surface of stent 50, which has ball 59. Respective sections of the flexible fiber are wound around catheter 57 in opposite directions one or more times to form band 52 and are half-knotted when the sections intersect, such as at intersection points 59. The ends of the flexible fiber are secured together with glue, preferably at a point closure 60 opposite to opening 58. A cross-sectional view of this arrangement is shown in FIG. 11.

Figure 12:
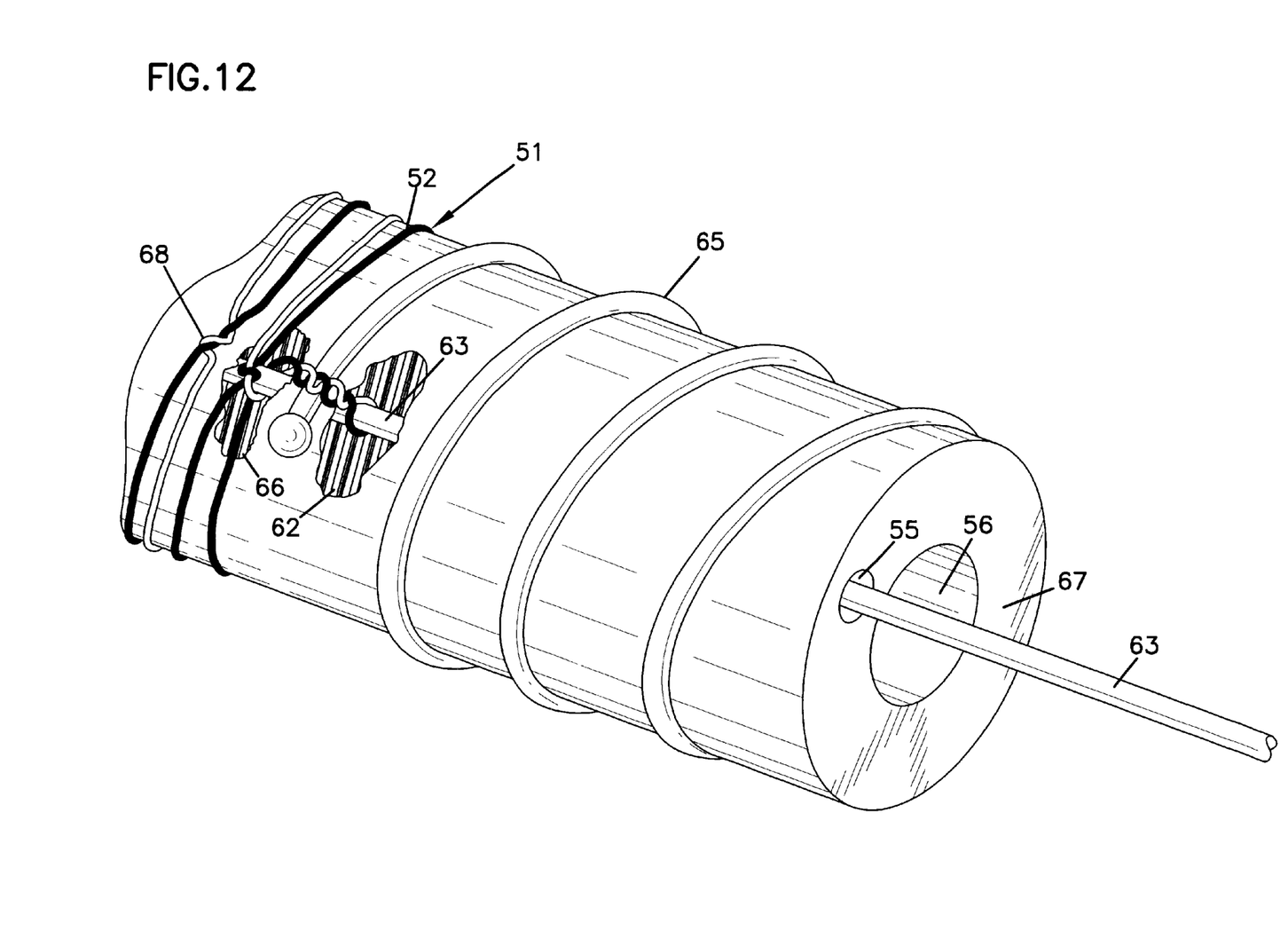

In FIG. 12 a continuous flexible fiber extends through opening 62 and is looped around release wire 63. Sections of the flexible fibers are intertwined to form a fixation member 64 that passes over the external surface of stent 65 and then into opening 66, where the intertwined sections loop under release wire 63. As the flexible fiber sections extend radially after looping around the release wire 63, they are half-knotted directly above release wire 63 and then separated to be independently and oppositely wound around catheter 67. The respective sections are half-knotted when they meet at intersection point 68, and the ends are fixed together with glue as in FIG. 11.

In operation either there is an additional lumen for another release wire or lumen 55 is large enough to contain two release wires that are operated independent of one another. One release wire would release the proximal and distal ends of stent 1, and the other release wire would release the middle section of stent 1, or one release wire will release the distal and middle sections and the other release wire will release the proximal section.

Figure 13:
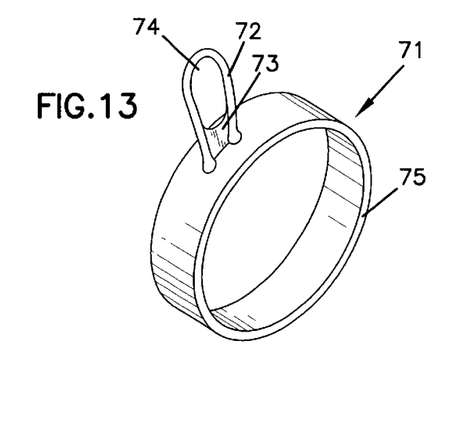
FIGS. 13, 14, 15, and 16 each represent a view of a release mechanism.

Another restraining mechanism 71 is shown somewhat more clearly in FIG. 13. Preferably fixation member .72 has a weld, solder, or glue member 73 that decreases the size of the opening 74 within fixation member 72, to ensure that a ball 59 at the end of the stent 50 does not become caught in said opening after stent deployment within the body duct.

Figure 14:
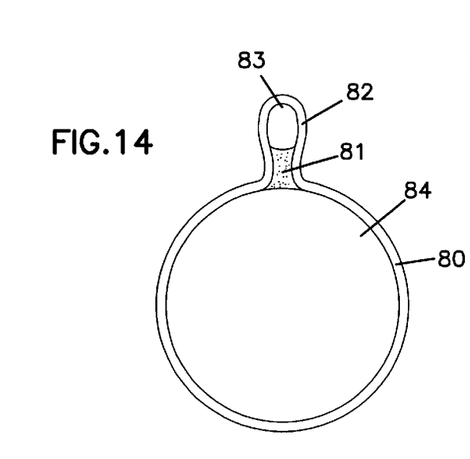
Figure 15:
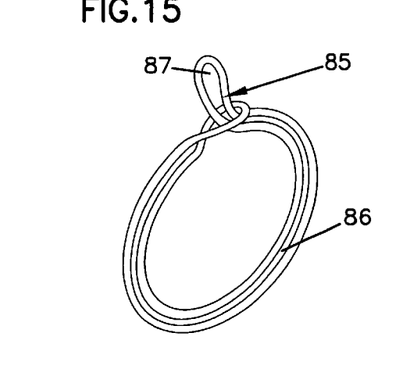

It would be appreciated by one skilled in the art that loop 72 and band 75 could have various functional equivalents, such as, for example, the embodiments shown in FIGS. 14 and 15. In FIG. 14, a continuous closed piece of metal or polymer wire 80 has a weld 81 that defines loop 82 with opening 83 and effective band member 84. Such a material could be comprised of any physiological acceptable or medically acceptable wire of appropriate flexibility, preferably having a diameter of from about 0.05 to 0.4 mm.

In the band or restraining mechanism shown in FIG. 15, a flexible strand of material has been arranged to define loop 85, with opening 87, and band 86. Such a strand could be comprised of any suitable flexible material such as silk, string, an appropriate polymer, or even small diameter solid or braided wire.

Figures 16, 16A, 16B, 16C:
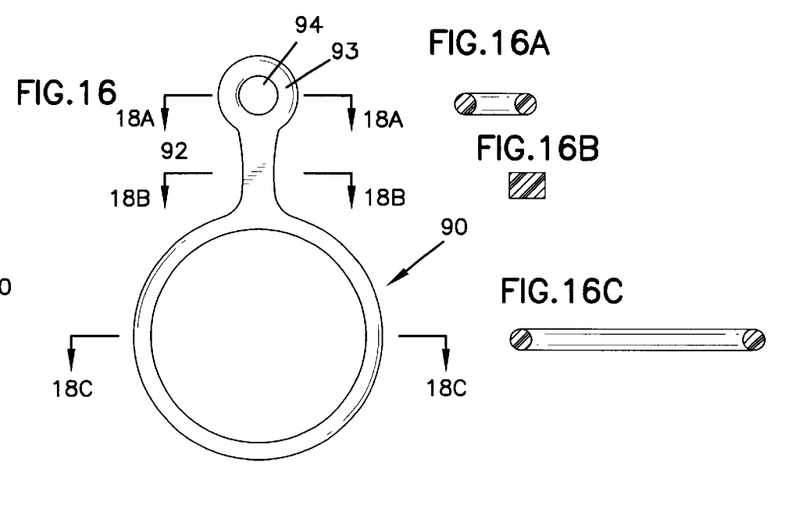
FIGS. 16A, 16B, and 16C represent cross-sectional views of portions of the release member of FIG. 16.

An additional embodiment of a restraining mechanism is shown in FIG. 16, wherein the restraining mechanism 90 comprises band 91, connector 92, and loop 93. Loop 93 defines opening 94. Preferably, band 91 and loop 93 have circular or oval cross-sections and connector 92 has a rectangular cross-section. Restraining mechanism 90 is preferably comprised of a suitable polymer or copolymer selected from the group consisting of nylon, polyethylene, polypropylene, polyvinylchloride, and co-polymers of one or more of these polymers. It is within the scope of the invention that restraining mechanism 90 could be comprised of two separate polymers; for example, band 91 would be made of a rigid polyethylene/polypropylene co-polymer whereas connector 92 and loop 93 would be made from a more flexible polymer such as polyethylene.

The catheters useful according to the invention must have at least one lumen suitable for release means, which lumen has two or more openings or sets of openings extending to the exterior surface of the catheter to permit interaction with fixation members. At each fixation point there may be 1 or 2 openings, dependent upon the release means employed. (Compare FIGS. 11 and 13.) The catheter may comprise a single, concentric, longitudinally extending lumen, or it may comprise one or more eccentric, longitudinally extending lumens.

In the cross-sectional view of FIG. 12, catheter 57 comprises main lumen 56 and side lumen 55, which contains release wire 54. Catheter 57 could instead comprise a single lumen 55, which could be eccentric or concentric within catheter 57. Also, the release wire-containing lumen could contain more than one release wire 54, possibly two or even three release wires if desired.

Figure 17:
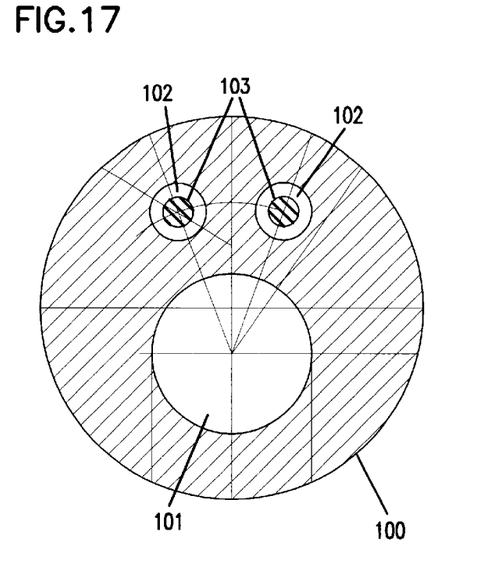
FIGS. 17 and 18 represent cross-sectional views of catheters useful according to the invention.
Figure 18:
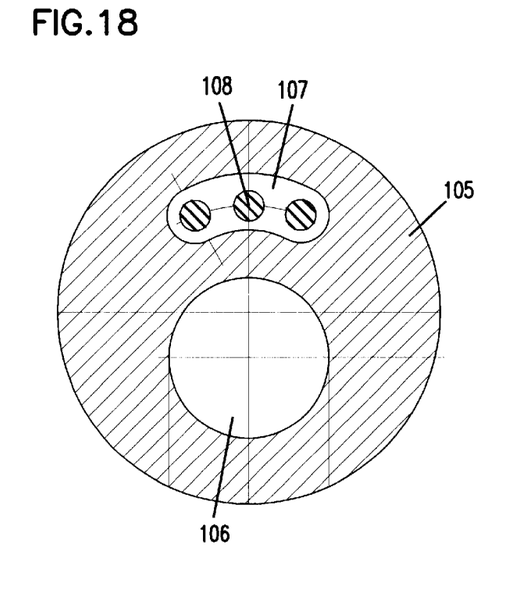

Additional cross-sectional views of catheters are shown in FIGS. 17 and 18. Catheter 100 comprises main lumen 101 and side lumens 102, the latter of which each may contain a release wire 103. Similarly, catheter 105 comprises main lumen 106 and side lumen 107, which latter lumen contains one to three release wires 108.

Figure 19:
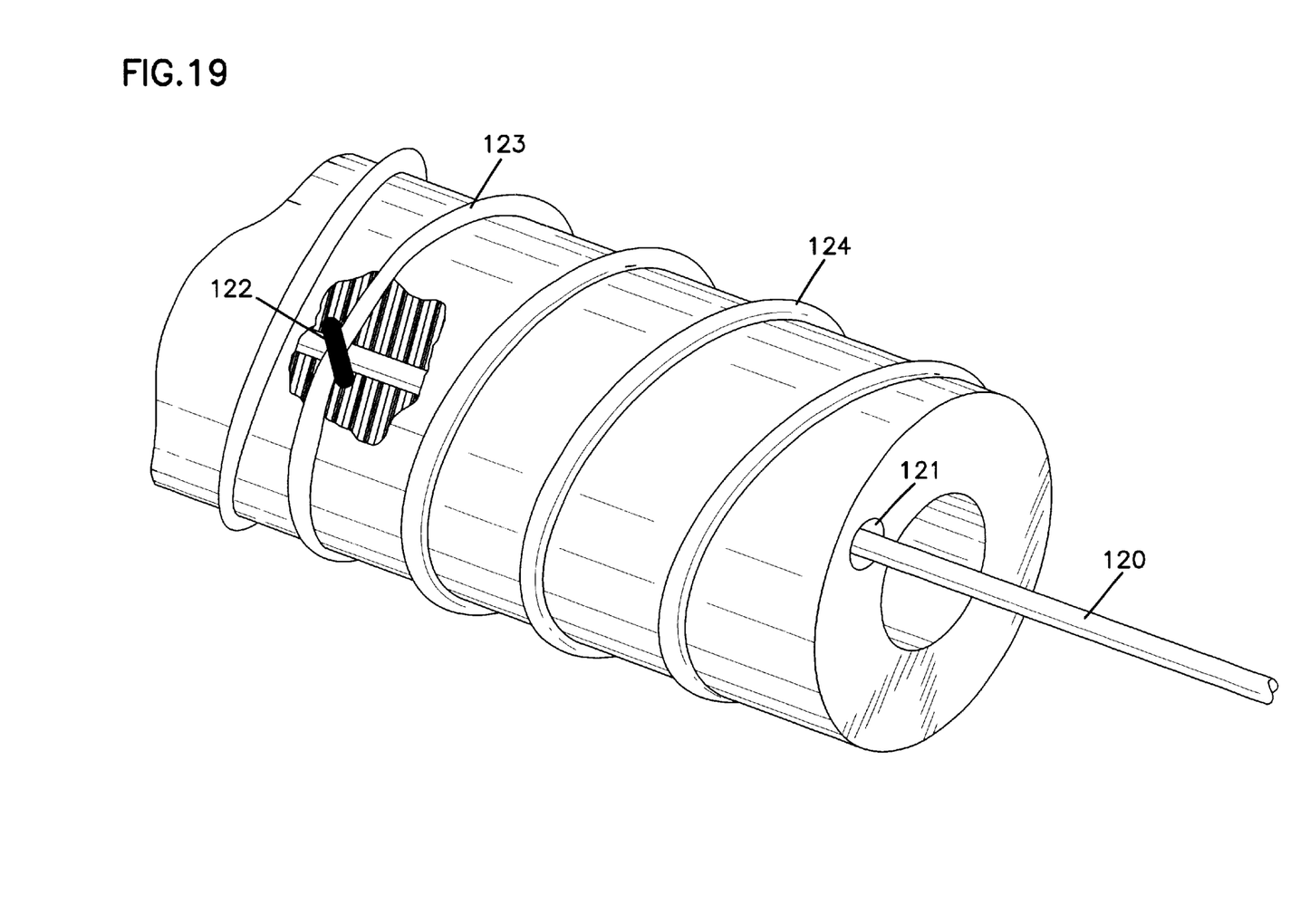
FIGS. 19 and 20 represent oblique, partially cross-sectional views of a fixation point.
Figure 20:
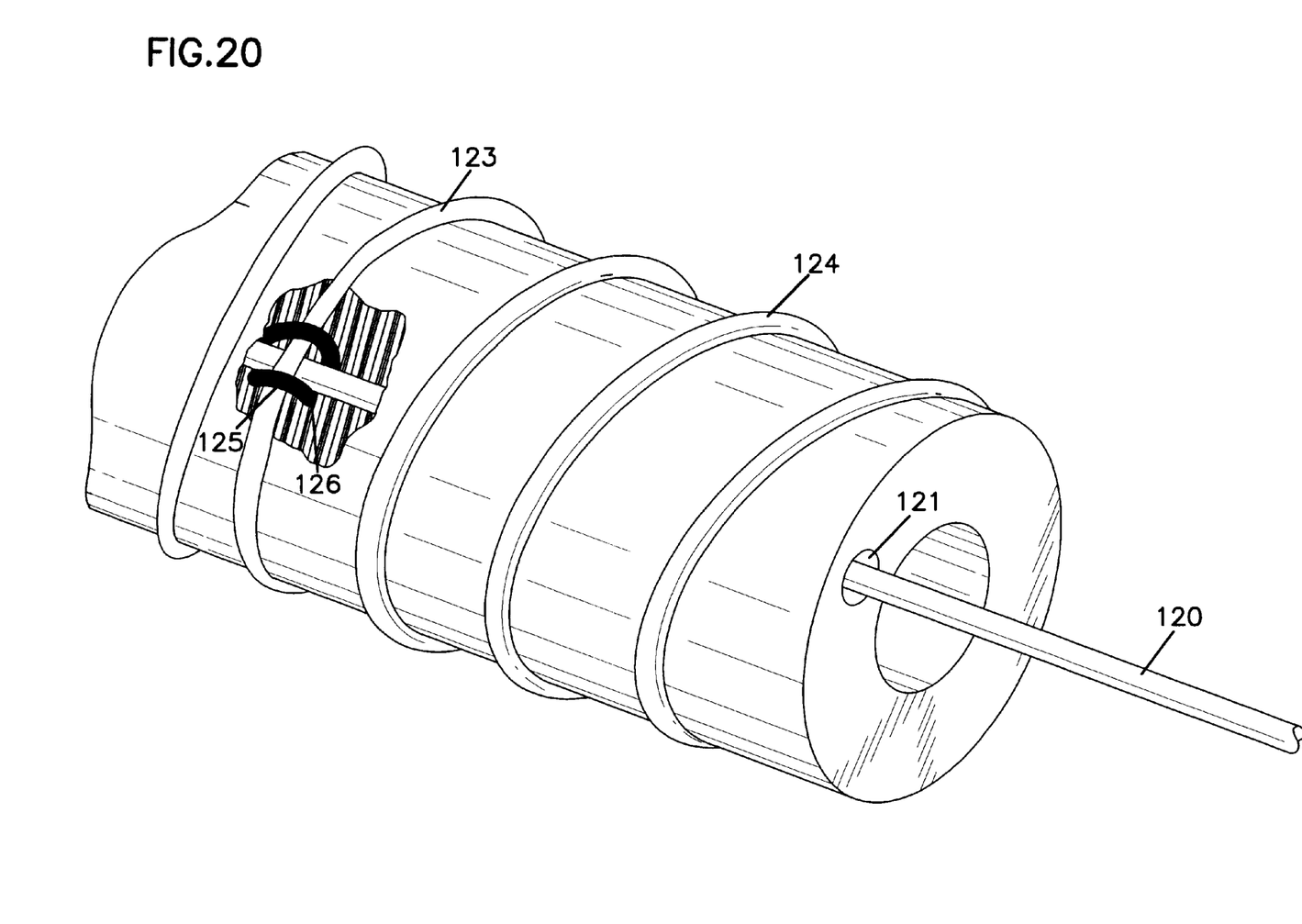

In some embodiments of the invention, especially a biliary stent, a middle restraining means is advantageous. However, because this stent can be closely wound even at its maximum, released diameter, the above-described arrangements are not necessarily as effective as desired. It has been found that a novel arrangement employing a bioabsorbable (or bioabsorbable) wire straining member is quite effective, particularly because the loops of the stent press the middle restraining means and prevent it from "jumping up," that is, away from the catheter surface. According to the embodiment of the invention set forth in FIGS. 19 and 20, a release wire 120 extends through side lumen 121 where it intersects bioabsorbable restraining member 122, which cooperates with release wire 120 to restrain stent member 123. Loop member 122 can be configured in two different ways: As shown in FIG. 19, restraining member 122 encompasses stent member 123, so that when release wire 120 is withdrawn proximally to release restraining member 122 and stent member 123, restraining member remains with stent member 123 or, if stent member 123 were a distal or proximal portion of stent 124, loop member 122 may disengage from stent 124. Alternatively, as shown in FIG. 20, restraining member 125 is configured so that the respective ends 126 of restraining member 125 are engaged by release wire 120. Therefore, when release wire 120 is pulled proximally, the ends 126 of restraining member 125 are disengaged from release wire 120, such that stent member 127 is also disengaged and stent 128 unwinds. Restraining member 125 may then dissociate from stent 128.

Restraining member 122 or 125 comprises a non-toxic, physiologically acceptable material that is preferably bioabsorbable. Therefore, whether the arrangement of FIG. 19 or FIG. 20 is employed, restraining member 122 or 125 will be absorbed by or passed through the body, and it will not matter if restraining member 122 or 125 remains engaged by the stent or not. Suitable materials are well known to those skilled in the art and would include other materials presently useful for other medical applications, including, but not limited to, the materials used in absorbable sutures such as homo- and copolymers of glycolic acid. See, for example, the materials disclosed in Kirk-Othmer, *Encyclopedia of Chemical Technology*, 2d Ed., Vol. 22, pages 433 et seq., incorporated herein by reference. Examples of such materials are DEXON™ PLUS and DEXONT™ "S", available from David+Beck, Inc. of Puerto Rico.

The stent delivery systems described herein are intended to be useful for the stents shown as well as other expandable stents. A preferred stent, such as that shown here, is described in detail in co-pending, commonly assigned U.S. patent applications Ser. No. 07/781,174, filed Dec. 11, 1991, and Ser. No. 07/827,031, filed Jan. 24, 1992, both of which are incorporated herein by reference.

More specifically, the preferred stent comprises a spatial spiral (helix) wound of wire of a material tolerated by the human body and which, furthermore, is not corroded or otherwise attacked by body fluids. Such a material, also known as a physiologically or medically acceptable material, could be one or more of several materials known for this purpose. Especially useful here are metals such as stainless steel, gold-plated medical grade stainless steel, stainless steel coated with silicone, bicarbon, or polytetrafluoroethylene, such as TEFLON®, tantalum, titanium, superelastic alloy such as nickel-titanium (Ni-Ti) alloys (commercially available as Nitinol or Tinel), a shape memory polymer, such as are described in U.S. Pat. No. 5,163,952, incorporated herein by reference, or bioabsorbable polymer material such as a saccharide or other biocompatible, non-toxic polymer taught by U.S. Pat. No. 5,141,516, incorporated herein by reference. The wire typically is circular in cross-section with a diameter of from about 0.1 to 1.0 mm, preferably from about 0.15 to 0.60 mm. Also, a wire cross-section of ellipsoidal, rectangular, rectangular with step, or S-shape geometry is suitable for stent production.

The preferred stent useful herein has thickened regions at the distal and proximal ends of the stent. In the text above reference is made to "ball 59"; however, each ball 59 can be spherical or non-spherical, so long as the "ball" functions as described. For example, in the embodiment shown in FIGS. 11 and 13, the "ball 59" could merely be a non-spherical thickened area, such as an egg, cone, or tear-drop shape, or a functionally equivalent loop, hole, or hook, that would cooperate with loop 53 to restrain an end of the stent. The ball 59 may be flattened on its inner and/or outer surface to facilitate the stent being in better contact with the outer surface of the catheter, to enable the mounted stent profile to be narrower.

The outer diameter and length of the stent will vary according to the intended use. For vascular or coronary use, the outer diameter of the wound stent will typically be from about 5 to 30 French (from about 1.7 to 10.0 mm), and the length of the stent can vary from about 2 to 15 cm, preferably from about 4 to 12 cm. It is also within the scope of the invention that the stent may comprise two spirals connected by a wire, the spirals and wire preferably being a continuous wire, or welding at respective distal and proximal ends.

A special property of nickel-titanium alloy (Nitinol) can be used for the production of the stent. Nickel-titanium alloy can have superelasticity at temperatures in the neighborhood of body temperature (37° C.). The term "superelasticity" is used to describe the property of certain alloys to return to their original shape upon unloading after substantial deformation. Superelastic alloys can be strained up to eight times more than ordinary spring materials without being plastically deformed. Such superelasticity would enable one to compress the stent to a very small diameter over the delivery catheter.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A stent delivery system for implanting a flexible, generally cylindrical, self-expanding stent, comprising:
    a catheter having distal and proximal ends, said catheter defining at least one lumen extending therethrough and having at least three longitudinally displaced openings or sets of openings extending from a lumen to the surface of the catheter;
    a flexible, self-expandable coiled stent in a form of a continuous helical coil with a uniform winding direction and voids defined between opposing turns of said coil, said stent having proximal and distal end sections separated by an intermediate section, said stent being wound circumferentially around said catheter defining a wound position with turns of the coil in at least a selected one of the proximal and distal sections being more closely wound with a narrower spacing between opposing turns than a winding and spacing between opposing turns in said intermediate section;
    said stent releasably secured to said catheter at proximal, distal and intermediate fixation points with said intermediate fixation point positioned at said intermediate section, said stent releasable from said wound position to an expanded position in a sequence with said selected one of said proximal and distal sections released from said catheter and expanded radially outward in response to said release prior to said intermediate section being released from said catheter at said intermediate fixation point.

2. A system according to claim 1 wherein both of said proximal and distal sections are more closely wound with a narrower spacing between opposing turns than a winding and spacing between opposing coils in said intermediate section.

3. A system according to claim 2 wherein said stent is releasably secured to said catheter with said stent releasable from said catheter in a sequence with said distal section released from said catheter prior to release of said proximal section from said catheter.

4. A system according to claim 1 wherein said intermediate section of said stent is in substantially the same position when said stent is in said wound position and said expanded position.

5. A stent deliverysystem for implanting a flexible, generally cylindrical, self-expanding stent, comprising:
    a catheter having distal and proximal ends and an outer surface, said catheter defining at least one lumen extending therethrough;
    a flexible, self-expandable coiled stent in a form of a continuous helical coil with a uniform wining direction and voids defined between opposing turns of said coil, said stent having proximal and distal end section separated by an intermediate section, said stent being wound circumferentially around said catheter defining a wound position with turns of the coil in both the proximal and distal sections being more closely wound with a narrower spacing between opposing turns than a winding and spacing between opposing turns in an other portion of said stent, said other portion of said stent including at least said intermediate section and having a predetermined longitudinal length when in said wound position;
    said stent releasably secured to said catheter with said stent releasable from said wound position to an expanded position in a sequence with said proximal and distal sections released first from said catheter and expanded radially outward in response to said release before said other portion of said stent is expanded radially outward, wherein said intermediate section is released from said catheter after said distal and proximal sections are released from said catheter, wherein a longitudinal length of said stent in said expanded position is not substantially less than said predetermined longitudinal length of said other portion of said stent; and
    said catheter including grooves formed on the outer surface of the catheter, the grooves corresponding to at least a section of the coil of the stent.

6. A method for deploying a stent using a delivery system, the delivery system including a catheter having a distal end and a proximal end, the catheter including a stent mounting location adjacent to the distal end, the delivery system also including a self-expandable coil stent mounted at the mounting location, the stent having a first end and a second end, wherein the first end is a proximal end of the stent and the second end is a distal end of the stent, the stent including coils having a first spacing adjacent the first end of the stent and also including coils at an intermediate location having a second spacing, the first spacing being narrower than the second spacing such that the coils are more closely wound at the first end, the method comprising:
    deploying the stent by initially releasing the first end of the stent such that the stent self-expands in a sequence that starts at the closely wound portion of the first end and moves along the length of the stent from the first end of the stent toward the second end of the stent; and releasing the second end of the stent after the stent has self-expanded.

7. The method of claim 6, wherein the first and second spacings between the coils change as the stent unwinds from the first end toward the second end.

8. The method of claim 6, wherein during self-expansion the coils of the stent are not restrained.

9. A method for deploying a stent using a delivery system, the delivery system including a catheter having a distal end and a proximal end, the catheter including a stent mounting location adjacent the distal end, the delivery system also including a coil stent mounted at the mounting location, the stent having a distal end and a proximal end, the stent including coils having a first spacing adjacent the proximal end of the stent and also including coils at an intermediate location having a second spacing, the first spacing being narrower than the second spacing, the delivery system also including a first release wire extending longitudinally through the catheter for releasing the proximal end of the stent from the catheter and a second release wire extending longitudinally through the catheter for releasing the distal end of the stent from the catheter, the method comprising:

delivering the stent with the catheter to a delivery site within a patient;

releasing the proximal end of the stent by pulling back the first release wire;

after the proximal end of the stent has been released, self-expanding the stent with the expansion of individual coils of the stent starting at the proximal end and moving along a length of the stent toward the distal end; and releasing the distal end of the stent after the stent has been self-expanded by pulling back the second release wire.

10. A delivery system comprising:

a catheter having a proximal end and a distal end, the catheter including a stent mounting location positioned adjacent the distal end, the catheter defining at least one lumen extending longitudinally there through, the catheter also defining at least one stent mounting opening defined adjacent to the stent mounting location, the stent mounting opening extending from the lumen to an outer surface of the catheter;

a self-expandable stent mounted at the stent mounting location of the catheter;

a stent retaining member for securing the stent to the catheter, the stent retaining member having a first end connected to the catheter adjacent to the stent mounting location, the retaining member also including a free end that loops over a portion of the stent and extends inwardly through the stent mounting opening to the lumen of the catheter; and a release wire that extends longitudinally through the lumen and that connects to the free end of the stent retaining member, where the stent is released from the catheter by pulling back on the release wire such that the release wire disengages from the stent retaining member thereby allowing the stent to self expand.

* * * * *